United States Patent [19]

Tomei

[11] Patent Number: 5,681,703
[45] Date of Patent: Oct. 28, 1997

[54] METHODS OF IDENTIFYING POTENTIALLY THERAPEUTICALLY EFFECTIVE AGENTS AND CELL STRAINS FOR USE THEREIN

[75] Inventor: L. David Tomei, Point Richmond, Calif.

[73] Assignee: LXR Biotechnology Inc., Richmond, Calif.

[21] Appl. No.: 471,785

[22] Filed: Jun. 6, 1995

Related U.S. Application Data

[62] Division of Ser. No. 366,368, Dec. 29, 1994, Pat. No. 5,637,486, which is a continuation of Ser. No. 56,439, Apr. 30, 1993, abandoned.

[51] Int. Cl.$^6$ ............................................. C12Q 1/68
[52] U.S. Cl. .................................. 435/6; 435/29
[58] Field of Search .................. 435/4, 29, 30, 435/32, 34, 240.1, 240.2, 240.21, 122.3, 6

[56] References Cited

U.S. PATENT DOCUMENTS 4,906,457  3/1990  Ryan ................................... 424/59

FOREIGN PATENT DOCUMENTS 63-51335  4/1988  Japan .

OTHER PUBLICATIONS

Wyllie, "Glucocorticoid-induced thymocyte apoptosis is associated with endogenous endonuclease activation" *Nature* (1980) 284:555–556.

Kanter et al., "Epidermal growth factor and tumor promoters prevent DNA fragmentation by different mechanisms" *Biochem. Biophys. Res. Commun.* (1984) 118:392–399.

Duke et al., "IL-2 addiction: withdrawal of growth factor activates a suicide program in dependent T cells" *Lymphokine Res.* (1986) 5:289–299.

Tomei et al., "Inhibition of radiation-induced apoptosis in vitro by tumor promoters" *Biochem. Biophys. Res. Commun.* (1988) 155:324–331.

Kruman et al., "Apoptosis of murine BW 5147 thymoma cells induced by dexamethasone and γ-irradiation", *J. Cell Physiol.* (1991) 148:267–273.

Yavelow et al., "Nanomolar concentrations of Bowman-Birk soybean protease inhibitor suppress X-ray-induced transformation in vitro" *Proc. Natl. Acad. Sci. USA* (1985) 82:5395–5399.

Bright et al., "Apoptosis: Programmed cell death in health and disease" *Bioscience Reports* (1994) 14:67–81.

Nowicki et al., "Nicotinamide and 3-aminobenzamide interfere with receptor-mediated transmembrane signaling in murine cytotoxic T cells: Independence of Golgi reorientation from calcium mobilization and inositol phosphate generation" *Cell. Immunol.* (1991) 132:115–126.

Sarin et al., "Protease inhibitors selectively block T cell receptor-triggered programmed cell death in murine T cell hybridoma and activated peripheral T cells" *J. Exp. Med.* (1993) 178:1693–1700.

Gong et al., "Different patterns of apoptosis of HL-60 cells induced by cycloheximide and camptothecin" *J. Cell. Physiol.* (1993) 157:263–270.

Tomei et al., "Apoptosis in C3H–10T ½ mouse embryonic cells: Evidence for internucleosomal DNA modification in the absence of double-stranded cleavage" *Proc. Natl. Acad. Sci. USA* (1993) 90:853–857.

Constantinides et al., "Functional striated muscle cells from nonmyoblast precursors following 5-azacytidine treatment" *Nature* (1977) 267:364–366.

Taylor et al., "Multiple new phenotypes induced in 10T ½ and 3T3 cells treated with 5-azacytidine" *Cell* (1979) 17:771–779.

Bright et al., *Bioscience Reports*, vol. 14, 1994, pp. 67–81.

Nowicki et al., *Cellular Immunology*, vol. 132, 1991, pp. 115–126.

Sarin et al., *J. Exp. Medicine*, vol. 178, 1993, pp. 1693–1700.

Gong et al., *J. Cellular Physiology*, vol. 157, 1993, pp. 263–270.

*Primary Examiner*—James S. Ketter
*Attorney, Agent, or Firm*—Morrison & Foerster

[57] ABSTRACT

The present invention is to a method of screening agents for potential therapeutic efficacy. The method comprises exposing a cell strain that is sensitive to apoptotic agents to known apoptotic agents and to a potential therapeutic agent. The cell strain is then cultured and cells are removed that display diminished adherence. The remaining, adherent, cells are then incubated in the presence of a proteinase to release proteinase sensitive cells. The proteinase sensitive cells are removed to yield proteinase resistant cells and the proteinase sensitive cells are counted. The proteinase resistant cells are then collected and counted. The agent is determined to have potential therapeutic efficacy if the ratio of proteinase sensitive cells to proteinase resistant cells changes relative to a control as a result of the presence of the agent.

16 Claims, 4 Drawing Sheets

METHODS OF IDENTIFYING POTENTIALLY THERAPEUTICALLY EFFECTIVE AGENTS AND CELL STRAINS FOR USE THEREIN

This application is a divisional of application Ser. No. 08/366,368 filed Dec. 29, 1994, now U.S. Pat. No. 5,637,486, which is a continuation of Ser. No. 08/056,434, filed Apr. 30, 1993 now abandoned.

FIELD OF THE INVENTION

The present invention is directed to methods to detect therapeutically effective agents, particularly those that affect apoptosis, mutagenesis, cellular proliferation and cellular differentiation.

BACKGROUND OF THE INVENTION

Apoptosis is a normal physiologic process that leads to individual cell death. This process of programmed cell death is involved in a variety of normal and pathogenic biological events and can be induced by a number of unrelated stimuli. Changes in the biological regulation of apoptosis also occur during aging and are responsible for many of the conditions and diseases related to aging. Recent studies of apoptosis have implied that a common metabolic pathway leading to cell death may be initiated by a wide variety of signals, including hormones, serum growth factor deprivation, chemotherapeutic agents, and ionizing radiation. Wyllie (1980) Nature, 284:555–556; Kanter et al. (1984) Biochem. Biophys. Res. Commun., 118:392–3999; Duke and Cohen (1986) nymphokine Res., 5:289–299; Tomei et al. (1988) Biochem. Biophys. Res. Commun., 155:324–331; and Kruman et al. (1991) J. Cell. Physiol., 148:267–273.

Although agents that affect apoptosis have therapeutic utility in a wide variety of conditions, it has not been possible to screen for these agents based on their apoptotic modulating activity. Such assays require a cell strain that can be maintained in vitro and retain sensitivity to apoptosis modulating signals. The vast majority of cell lines used to screen agents are selected for their ability to be maintained in vitro. Cells that are most easily maintained are "transformed" cells that have lost the ability to undergo apoptosis and are thus unsuitable for use in screening apoptosis modulating agents. Although cell strains such as the mouse embryonic C3H-10T1/2 type have been shown to be sensitive to such agents, it has not been possible to perpetuate a phenotypically stable strain of these cells beyond 120–140 population doublings. Thus, it has been impossible to obtain the reproducible results necessary to engineer a high through-put replicate culture assay for drug screening.

It has now been found that, by the method described herein, cell strains sensitive to apoptotic agents can be used to provide reproducible results in screening for agents that modulate a wide variety of disorders. These phenotypically stable cell strains can now be maintained for at least 900 population doublings. Moreover, by utilizing the parameters of the screening assay, new, improved cell strains can now be obtained that are suitable for use in the screening assays and for studying apoptosis.

SUMMARY OF THE INVENTION

The present invention is directed to a method of screening agents for potential therapeutic efficacy. The method comprises culturing a cell strain that is sensitive to apoptotic modulating agents for a period of time and under conditions sufficient to attain exponential proliferation activity without density-dependent constraints at any time during the assay. The cell strain is then exposed to conditions that are known to induce apoptosis and either simultaneously or shortly thereafter exposed to an agent to be screened. The cell strain is cultured for a time and under conditions suitable to attain a density of about one population doubling from density-dependent arrest of cell cycle. Cells that display diminished adherence are then removed and enumerated. The remaining adherent cells are then incubated in the presence of a proteinase for a time and under conditions suitable to release proteinase sensitive cells from the adhesion surface. The proteinase sensitive cells are removed and enumerated to yield the remaining proteinase resistant adherent cells. The proteinase resistant cells are then incubated for a time and under conditions suitable to release the cells. The released cells are collected and enumerated.

It is possible that treatment of certain diseases requires that therapeutic agents either specifically induce apoptosis in instances where deletion of cells is believed to be therapeutically effective such as in the treatment of cancer. Inhibition of apoptosis is preferred in instances where prevention of cell loss is believed to be therapeutically effective such as in prevention of ionizing radiation-induced cell death in the gastrointestinal system. The agent is determined to have potential anti-apoptotic therapeutic efficacy if the number of non-adherent cells is reduced relative to the number of non-adherent cells in the control, and the number of proteinase resistant cells increases relative to a control. The agent is determined to have apoptosis inducing therapeutic efficacy if there is an increase in the number of non-adherent cells relative to the number of non-adherent cells in the control.

The method can also be used to obtain and maintain phenotypically stable cell strains suitable for use in the screening assay or any other assay requiring cells that are responsive to apoptosis inducing and apoptosis inhibiting agents.

BRIEF DESCRIPTION OF THE DRAWINGS

FIG. 2 is discussed in Example 3.

FIG. 3 is discussed in Example 3.

FIG. 4 is discussed in Example 3.

DETAILED DESCRIPTION OF THE INVENTION

1. Screening Assay

Figure 1:
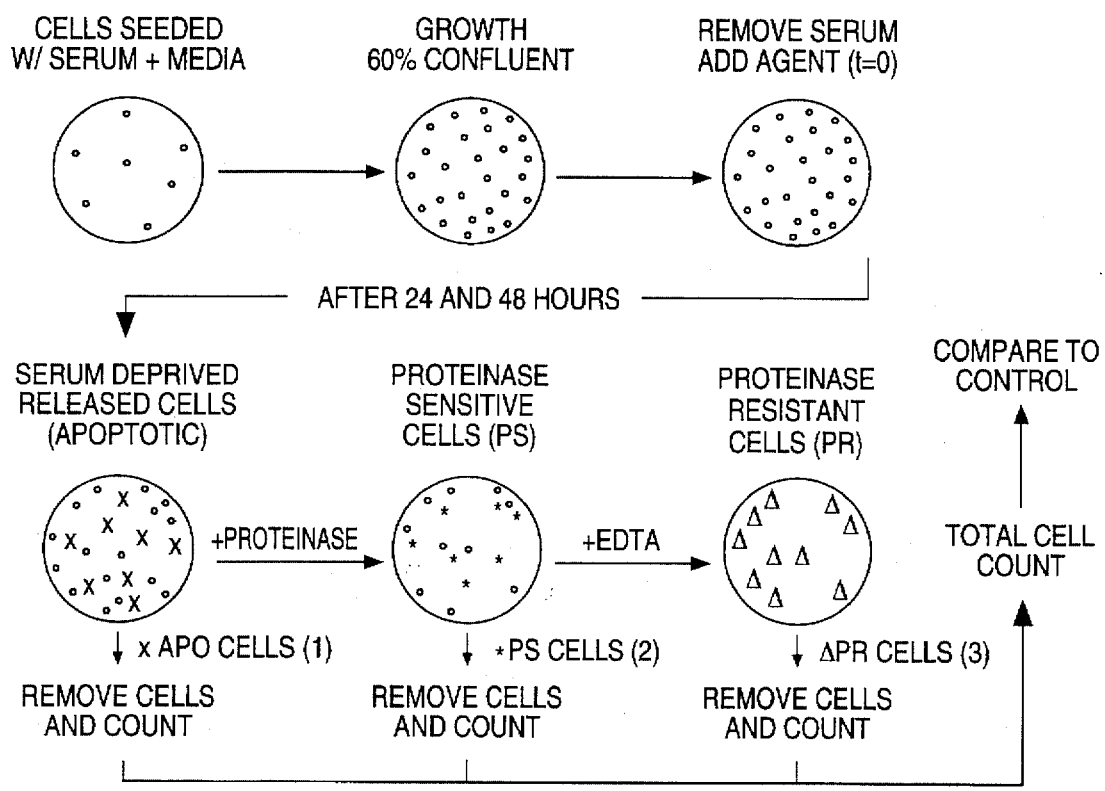
FIG. 1 is a flow chart of the cell culture method described in Example 1.

The present invention is to a method of screening agents for potential therapeutic efficacy. The method comprises providing a cell strain that is sensitive to apoptotic agents; culturing the cell strain for a time and under conditions sufficient to attain exponential proliferation without density dependent constraints at any time during the assay; exposing the cell strain to conditions that are known to induce apoptosis; exposing the cell strain to an agent to be screened; culturing the cell strain for a time and under conditions suitable to attain a density of about one population doubling from density-dependent arrest of cell cycle; removing and enumerating cells that display diminished adherence. The remaining adherent cells are then incubated in the presence of a proteinase for a time and under conditions suitable to release proteinase sensitive cells from the adhesion surface. The proteinase sensitive cells are removed and enumerated to yield the remaining proteinase resistant adherent cells. The proteinase resistant cells are then incubated for a time and under conditions suitable to release the cells. The released cells are collected and enumerated.

The agent is determined to have potential therapeutic efficacy if the number of non-adherent cells is reduced relative to the number of non-adherent cells in the control, and the number of proteinase resistant cells increases relative to a control.

The cell strain is obtained from pluripotent embryonic cells with stable, normal, intact, phenotypes. The cell strain is an adherent strain, its in vitro growth is dependent on anchorage to the solid support on which it is grown.

Preferably, the cell strain has the following characteristics: density dependent regulation of proliferation and death; pluripotent and capable of demonstrating at least two distinct differentiated cell types upon suitable stimulus; sensitive to loss due to transformation induced by carcinogenic and oncogenic agents such as DNA damaging agents or various oncogenic viruses; response to agents that both induce and block proliferation, differentiation, and apoptosis; ability to exhibit apoptotic cell death as marked by ultrastructural changes of chromatin and specific changes in the molecular structure of DNA associated with apoptotic DNA degradation. More preferably the cell strain is the mouse embryonic C3H-10T1/2 clone 8. This cell strain is available from the American Type Culture Collection under accession number ATCC CCL 226 and is designated $C_3H$-10T1/2, clone 8. C3H10T1/2 has also ben described for use in transformation experiments. Yavelow et al. (1985) Proc. Natl. Acad. Sci. USA, 82:5395–5399.

The initial culturing step is to attain stable exponential proliferation without density dependent constraints at any time during the assay. In the case of C3H-10T1/2, this is for about 5 days at 37° C. with a gas overlay of 5% $CO_2$ in a suitable growth medium. Although the optimal medium will vary depending on the cell strain used, in the case of C3H-10T1/2, the preferred medium is Eagle's basal medium with Hank's salts (BME) supplemented with 10% (v/v) heat-inactivated fetal bovine serum. In the case of C3H-10T1/2, after five days of incubation, the cells have reached about seventy-five percent confluency. Although this is the preferred confluency, particularly for C3H-10T1/2, the confluency can be greater or lesser so long as statistically significant results are obtained. Although the optimal confluency for each cell strain is derived empirically, this is a straightforward determination based on the parameters discussed below.

Incubating the cells so that they maintain exponential proliferation without density dependent constraints during the assay prevents artificial skewing of the results. This is because once the cells reach a certain density, exponential proliferation ceases and the cells become quiescent. The density at which quiescence occurs is unique to each cell strain and is empirically derived by measuring indicia of cell division such as manufacture of DNA. Quiescent cells do not respond to apoptotic and anti-apoptotic agents and thus provide erroneous results.

The level of confluency reached before adding the apoptotic agent depends only on maintenance of the exponential growth phase and attaining a statistically significant number of cells. In the case of C3H-10T1/2, seventy-five percent confluency is preferred. The optimal confluency for any strain is empirically derived.

The condition that induces apoptosis in the cells after the initial incubation step includes but is not limited to serum deprivation, growth factor deprivation, ultraviolet radiation, γ-radiation, soft β-radiation, hypo-osmotic shock, chemotherapeutic agents, or specific receptor mediated agents. In the case of C3H-10T1/2, the preferred method of inducing apoptosis in a reproducible portion of the cell strain in replicate cultures is to replace the serum-supplemented growth medium with serum-free growth medium. After the change to serum-free medium, the cells are incubated for a time and under conditions suitable to maintain exponential proliferation without density dependent constraints in suitable replicate control cultures. In the case of C3H-10T1/2, the conditions are for about 20 hours at 37° C. in an atmosphere of 5% $CO_2$.

Culturing of cells is dependent upon fetal bovine serum supplement to the synthetic growth medium. It is important to preserve both the growth promoting potential of serum supplements as well as the sensitivity to apoptosis inducers. It has now been found that serum production lots vary not only with respect to proliferative potential, but also with respect to the ability of the serum to promote apoptosis responsiveness in the cells. This aspect of the assay is counter-intuitive in as much as conventional serum screening tests used in the art are based primarily upon determining the relative ability of various production batches of animal sera to maintain high viability or survival rates of various reference cell cultures. Contrary to that rationale, the apoptosis assay serum screening test determines the relative ability of various serum production batches to yield apoptotic, or dying and dead cells upon withdrawal of the growth medium. Thus, each serum lot must be selected from a screened group of several lots in order to ensure preservation of the cell strain responsiveness to both apoptosis inducers and inhibitors.

The agents to be assayed are introduced to the cells either simultaneously with or shortly after induction of apoptosis. Although the time of introduction will vary according to the cell strain used and the method of induction of apoptosis, the optimal parameters can be determined empirically and applied in a routine basis thereafter. In the case of C3H-10T1/2, the agent to be assayed is added simultaneously with induction of apoptosis.

After addition of the putative therapeutic agent, the cells are further incubated for a time sufficient to display apoptosis. At that time, a certain proportion of the cells in each replicate culture display rounding and loss of flattened shape, diminished adherence and are removed by a mild shearing effected by washing with a suitable buffered salt solution.

After the nonadherent cells are removed and enumerated, the remaining adherent cells are comprised of proteinase sensitive and proteinase resistant cells. It has now been found that the proteinase sensitive cells are the population that contains the cells that would have otherwise died by apoptosis in the absence of an effective apoptosis inhibitor. The proteinase sensitive cells are removed for enumeration by incubation with a suitable proteinase. A suitable proteinase is trypsin. Trypsin is the standard proteinase for removing adherent cells; however, any proteinase that effectively removes proteinase sensitive cells without damaging the cells removed or the remaining proteinase resistant cells is suitable for use in the present invention.

In the case of C3H-10T1/2, the adherent cells are incubated in the presence of concentrations of about 1 mg/ml to 1 µg/ml trypsin for about 10 minutes with gentle shaking at room temperature and are removed by washing. The proteinase sensitive cells are then enumerated by a suitable method.

Suitable enumeration methods include but are not limited to direct physical counting, electronic particle counting and fluorescence staining to measure DNA. Any cell counting means known in the art is suitable for use in the present invention.

The proteinase resistant cells are then released. Preferably, release is accomplished by incubation in the presence of an agent that decreases the calcium concentration to a level sufficient to release the cells. Such agents include but are not limited to calcium chelators such as ethylenediaminetetraacetic acid and ethylene glycol-bis(β-amino-ethyl ether) N,N,N',N'-tetraacetic acid.

The number of agents suitable for assaying for therapeutic effectiveness is virtually limitless and can be obtained from a variety of chemical, nutritional and biological sources. For instance, suitable chemical agents can be novel, untested chemicals, as well as agonists, antagonists, or modifications of known therapeutic agents. Nutritional agents can be complex extracts from plant or animal sources or extracts thereof. Such agents can be easily derived from plant sources such as soy, pea, or potato by-products, or from animal products such as whey or other milk byproducts. Biological agents include biological response modifiers, antibodies and other small molecules. Such small molecules can be either derived from biological sources or chemically synthesized to mimic the effect of biological response modifiers.

The assay is suitable for use in a high throughput format, thus enabling the screening of large numbers of agents in a range of concentrations. Most therapeutic agents screened to date have been effective in a concentration of about 1 µg/ml, although a wide range of concentrations can be screened. Preferably, the range of concentrations is from 1 ng/ml to 1 mg/ml. The upper range is limited by solubility of the agent and the lower range is not necessarily limited but should be in a therapeutically effective range.

The assay is preferably performed in standard tissue culture 60 mm Petri dishes which have about 20 cm$^2$ surface area. Although the assay may be scaled down to 2 cm$^2$ tissue culture dishes, it is not suitable for use in microtiter plates having significantly lower growth surface areas. The cell strain must be maintained as a spatially random distributed population that can not be maintained in the small surface area of a microtiter dish.

A positive response to the agents is clear. Typically the agents found to have therapeutic efficacy by decreasing apoptosis have been found to increase proteinase resistant cells in a statistically significant manner. These agents also statistically reduce the number of non-adherent, apoptotic cells.

It has also now been shown that agents that reduce the number of non-adherent cells may do so through a non-specific action unrelated to reduction of apoptosis. Thus, merely measuring the number of non-adherent adherent cells that appear in replicate treated cultures is subject to error in the form of false positive results and is insufficient for the screening assay. For instance, toxic agents that may rapidly damage cells and lead to disintegration of the cells may be falsely determined to reduce the appearance of apoptotic cells by virtue of the reduction in non-adherent cell counts. This has now been found to be an avoidable error if proteinase resistant cells are simultaneously determined in the replicate cultures. Also, enumeration of a proteinase resistant cell number is inherently more reliable than measurement of a loss of cells by a subtraction method.

The cell strain utilized in the assay is particularly sensitive to apoptosis inducers and inhibitors and is therefore useful in identifying agents with therapeutic efficacy in treating diseases and conditions related to aging and cellular differentiation. These conditions and diseases include but are not limited to cardiovascular disease, cancer, immunoregulation, viral diseases, anemia, neurological disorders, diarrhea and dysentery, diabetes, hair loss, rejection of allografts, prostrate hypertrophy, obesity, ocular disorders, stress, and the aging process itself.

The assay is not limited to diseases and conditions related to aging, however, as the list above indicates, many conditions associated with aging may also be the result of illness or other physical insults. For instance, while not related to aging per se, the trauma induced by head and spinal cord injuries results in apoptotic events that cause the subsequent cellular loss and the consequent exacerbation of paralysis in many patients. Agents useful in preventing apoptosis will be useful in minimizing such paralysis.

It has now been found that the assay further distinguishes between agents that have therapeutic utility and those that block apoptosis but are toxic. By comparing the proportion of apoptotic, proteinase sensitive and proteinase resistant cells, the assay detects those agents that modulate proteinase sensitivity (the apoptosis marker) rather than those agents that merely decrease the number of nonadherent (dead) cells.

The assay further provides the means to determine effects of agents on proliferation such as those which have mitogenic activity in addition to anti-apoptotic activity.

2. Method of Obtaining Suitable Cell Strains for the Screening Assay

The invention further provides a method of obtaining cell strains other than C3H-10T1/2 that retain responsiveness to apoptosis modulating agents. The method, similar to that above, comprises obtaining a cell sample; culturing the cell sample for a time and under conditions sufficient to maintain exponential proliferation without density dependent constraints; exposing the cell sample to conditions that induce apoptosis; treating the cell sample with an agent known to induce proteinase resistance; culturing the cell sample for a time and under conditions suitable to attain a density of about one population doubling from density-dependent arrest of cell cycle; removing cells that display diminished adherence to yield adherent cells; exposing the adherent cells to a proteinase; incubating the adherent cells for a time and under conditions suitable to release proteinase sensitive cells; and collecting the remaining proteinase resistant cells. These protease resistant cells are then retained and passaged to generate a stable cell strain that continues to express responsiveness to apoptosis inducers and inhibitors.

The preferred treatment of cells for maintenance of apoptosis responsiveness is 12-O-tetradecanoyl phorbol-13-acetate (TPA) at a concentration of about $10^{-9}$ to $10^{-8}$ molar and commercially available from Sigma Chemical Company and others.

The incubation conditions and other parameters are essentially similar as those described for the assay described above.

The cell sample is preferably obtained from pluripotent embryonic cells with a normal, intact, phenotype. The species the cell sample is derived from is not as important as the embryonic origin of the cells. This is because embryonic cells are controlled by highly conserved, common proteins that exhibit minimal species specific variations important to adult organisms. The cell strain should not be transformed, that is, should not be a so-called "immortalized" or tumorigenic cell line. Such immortal cell lines have lost most or all of their ability to respond to apoptosis modulating signals or agents.

3. Method of Passaging the Cell Strain

The invention further provides a method of passaging the cell strains so as to preserve phenotypic fidelity defined in part but not completely by cellular responsiveness to apoptosis modulating agents. The method comprises culturing a cell strain that is sensitive to apoptotic modulating agents for a time and under conditions sufficient to attain exponential proliferation activity without density-dependent constraints at any time during the method. The cell strain is then exposed to conditions that are known to induce apoptosis. The cell strain is cultured for a time and under conditions suitable to attain a density of about one population doubling from density-dependent arrest of cell cycle. Cells are then removed that display diminished adherence and enumerated. The remaining adherent cells are then incubated in the presence of a proteinase for a time and under conditions suitable to release proteinase sensitive cells from the adhesion surface. The proteinase sensitive cells are removed and enumerated to yield the remaining proteinase resistant adherent cells. The proteinase resistant cells are then incubated for a time and under conditions suitable to release the cells. The released cells are collected and enumerated.

The incubation conditions and other parameters are essentially similar as those described for the assay described above.

The following examples are provided to illustrate but not limit the claimed invention. The examples describe the identification of therapeutically effective agents by the use of the present invention.

EXAMPLES

Example 1

Cell Culture Techniques

FIG. 1 depicts a flow chart of the basic technique of cell culture for the assay. The following is a more detailed description of the assay as performed using C3H-10T1/2 clone 8 mouse embryonic cells.

The cells are obtained at the lowest available serial passage level preferably less than level 11. The phenotypic characteristics of the cells are verified as meeting the following criteria. Standard cell culture techniques are used.

1. Confirmation of a mean doubling time of 22 (±2) hours under standard conditions of basal Eagle's growth medium supplemented with 10% (v/v) fetal bovine serum in plastic culture flasks maintained at 37° C. in a humidified atmosphere of 5% $CO_2$.

2. Cloning efficiency determined to be 25% (±2) at densities of 200 cells/20 $cm^2$ under standard growth conditions.

3. Saturation cell density confirmed to be $5\times10^5$ ($\pm2\times10^5$) cells/20 $cm^2$ plastic petri dish under standard growth conditions.

4. At saturation cell density, it is confirmed that more than 98% of cells are in the $G_1$ phase of the cell cycle.

5. The morphology of exponentially proliferating cultures is radically changed at saturation density such that the spindle shaped cells having extensive overlapping and lack of parallel orientation during exponential proliferation changes to wide, flat epithelioid monolayer without distinct intercellular demarcation and no overlapping.

6. Cells are sensitive to malignant transformation by chemical carcinogens, typically 3-methyl cholanthrene, or ultraviolet irradiation yielding transformed foci.

7. Cells do not form a fibrosarcoma tumor when injected at levels of $10^5$ cells subcutaneously in the suprascapular region of syngeneic animals, whereas, following malignant transformation in vitro, tumors are observed under similar conditions.

The cells are then cultured in containers that are typically 60 mm diameter plastic petri dishes specially prepared for mammalian cell culture and are commonly available from several commercial sources.

Cells for replicate culture are obtained from stock cultures which are confirmed to be in exponential phase proliferation and not in post-confluent saturation density to ensure that cells are not arrested in the $G_1$ phase of the cell cycle.

The cells are seeded onto each plate in a volume of 5 ml complete growth medium in which are suspended a standardized number of cells. The standardized number should be not less than $10^3$ but not greater than $10^4$ cells.

Special care must be taken to ensure that cells are uniformly distributed over the surface of each culture dish in order to prevent clustering of cells during subsequent growth which results in non-uniform increases in cell densities and premature saturation densities in limited regions on each dish. Premature saturation density in limited regions results in serious errors in assay results.

Growth medium is renewed each 48 hours.

When cell density reaches approximately 70% uniformly across each dish surface, which typically corresponds to a density of $1\times10^5$ to $3\times10^5$ cells/dish, the complete growth medium is removed by aspiration and replaced with fresh serum-free growth medium.

Drugs or agents to be assayed can be premixed into the serum-free medium, or added in appropriately small volumes immediately after the medium change.

Typically, in order to ensure statistical reliability, each agent or specific treatment is performed on at least four replicate cultures and appropriate controls are also incorporated.

After a standardized period of incubation at 37° C. under humidified 5% $CO_2$ atmosphere of between 3 hours and 72 hours, typically 24 hours, each plate is prepared for measurement of responses.

The following measurements are performed:

1. All non-adherent or loosely adherent cells are removed from the culture dish and measured by appropriate techniques typically counting by electric particle counting instrument.

2. The remaining adherent cells are exposed to a buffered (typically pH 7.3) balanced salt solution such as Hanks Balanced Salt Solution containing a standardized concentration of the enzyme trypsin. The trypsin concentration is typically 0.1 mg/ml but can be between 1 and 0.001 mg/ml, typically in a volume of 1 ml.

Each culture is incubated either at ambient temperature or 37° C. on a rocking platform to ensure uniform distribution of the trypsin reagent over the culture surface. After a standardized period of typically 10 minutes, the released cells are removed from each dish, and measured by the same means described above, typically electronic particle counting. This measurement is referred to as the serum deprivation released or SDR count and typically contains at least 98% apoptotic cells.

The remaining adherent cells in each dish are then released by exposure to a buffered solution containing a calcium ion chelating agent typically EDTA typically at a concentration of 2 mg/ml. This measurement is referred to as the proteinase sensitive or PS count and typically contains the cells that would have otherwise died by apoptosis in the absence of an effective inhibitor.

The final cells remaining adhered to the solid support are then immediately dispersed and removed from the dish for measurement by the same means used in previous measurements, typically electronic particle counting. This measurement is referred to as the proteinase resistant or PR count and typically contains cells that express the property of resistance to proteinase-induced shape change which has been identified to be a critical specific expression related to control of apoptosis.

Each cell count is typically performed in duplicate on each of four replicate dishes for each experimental treatment group and control. The statistical significance of this is shown in Example 4.

Final data are initially expressed as the mean cell number and standard deviation of the mean according to conventional statistical data-analysis as discussed in Example 4. The results obtained are shown in Table 1. The numbers in Table 1 printed in bold print represent the numbers used in Table 2 as described in Example 2. In Table 1, the data are reported as cells/plate x 10,000. The abbreviations used are: SD, standard deviation; PR, proteinase resistant cells; and PS, proteinase sensitive.

A preferred positive result is typically dependent upon a statistically significant reduction of SDR cells in combination with a statistically significant increase in PR cells, However, putative apoptosis modulating agents can produce either reduction of SDR cells or increased PR cells and should be considered to be positive and warranting further consideration. Agents that produce either increased SDR or decreased total cell counts (i.e., SD+PS+PR) should be considered to be potentially cytotoxic at the concentrations applied. A negative outcome would be failure to observe changes in either SDR or PR counts at concentrations determined to be non-toxic.

Example 2

Bovine Serum Screening Test

The purpose of screening the bovine serum used as a supplement to the synthetic portion of the cell culture growth medium is to determine the best manufacturer's production batch in terms of optimal assay performance. This aspect of the assay is counter-intuitive in as much as conventional serum screening tests used by those skilled in the art are based primarily on determining the relative ability of various production batches of animal sera to maintain high viability or survival rates of various reference cell cultures. Contrary to that rationale, the apoptosis assay serum screening test determines the relative ability of various serum production batches to yield apoptotic, or dying and dead, cells upon withdrawal from the growth medium.

As an example, Tables 1 and 2 present typical data obtained in the process of screening 5 different bovine serum production batches obtained from a commercial source. These are listed as Lots 1 through 5. In order to distinguish between necrotic and apoptotic cells, cells are treated with TPA. Two independent variables to be measured are the number of apoptotic cells in the untreated control cultures

TABLE 1

| | Bovine serum screening test C3H-10T1/2 cells | | | | | | | | | | |
|---|---|---|---|---|---|---|---|---|---|---|---|
| | Apoptotic | +/−SD | % control | PR | +/−SD | % control | PS | +/−SD | % control | Total | % control |
| Lot #1 Control | 22.6 | 2.6 | 100.0 | 17.7 | 3.6 | 100.0 | 20.4 | 3.3 | 100.0 | 60.7 | 100.0 |
| 1 nM TPA | 19.8 | 0.6 | 87.7 | 27.8 | 4.4 | 157.1 | 16.7 | 2.6 | 81.9 | 64.3 | 105.9 |
| 10 nM TPA | 13.1 | 1.5 | 58.0 | 48.1 | 4.4 | 271.8 | 15.9 | 1.2 | 77.9 | 77.1 | 127.0 |
| Lot #2 Control | 13.6 | 0.5 | 100.0 | 17.2 | 2.1 | 100.0 | 20.2 | 1.8 | 100.0 | 51.0 | 100.0 |
| 1 nM TPA | 10.4 | 1.6 | 76.5 | 23.5 | 3.3 | 136.6 | 15.0 | 1.8 | 74.3 | 48.9 | 95.9 |
| 10 nM TPA | 6.0 | 0.4 | 44.1 | 35.6 | 2.7 | 207.0 | 14.2 | 1.3 | 70.3 | 55.8 | 109.4 |
| Lot #3 Control | 30.8 | 2.0 | 100.0 | 16.7 | 5.1 | 100.0 | 25.9 | 5.2 | 100.0 | 73.4 | 100.0 |
| 1 nM TPA | 25.4 | 1.3 | 82.5 | 26.3 | 4.5 | 157.5 | 22.3 | 2.8 | 86.1 | 74.0 | 100.8 |
| 10 nM TPA | 15.4 | 1.5 | 50.0 | 49.5 | 1.8 | 296.4 | 13.3 | 1.2 | 51.4 | 78.1 | 106.4 |
| Lot #4 Control | 35.9 | 1.9 | 100.0 | 20.5 | 1.0 | 100.0 | 34.6 | 0.9 | 100.0 | 90.9 | 100.0 |
| 10 nM TPA | 21.6 | 4.9 | 60.2 | 42.6 | 6.5 | 207.8 | 45.0 | 3.4 | 130.1 | 110.1 | 121.1 |
| 50 nM TPA | 16.8 | 1.4 | 46.8 | 47.4 | 4.2 | 231.2 | 45.9 | 4.1 | 132.7 | 109.1 | 120.0 |
| Lot #5 Control | 49.1 | 6.0 | 100.0 | 20.5 | 4.2 | 100.0 | 49.6 | 2.5 | 100.0 | 119.2 | 100.0 |
| 10 nM TPA | 30.7 | 5.1 | 62.5 | 53.9 | 2.5 | 262.9 | 47.0 | 4.9 | 94.8 | 131.6 | 110.4 |
| 50 nM TPA | 16.7 | 2.4 | 34.0 | 55.6 | 6.7 | 271.2 | 52.2 | 3.2 | 105.2 | 124.5 | 104.3 |

Initial data-analyses for assay reliability should reveal that variations among replicate culture dishes for any of the three measurements should not be greater than 7% standard deviation. Data can be normalized by expressing the individual counts of SDR, PS, and PR as ratios to the corresponding value determined in control dishes.

compared with replicate cultures treated with TPA. These variables are the released cell or Apoptotic count, and the proteinase-resistant or PR cell count as shown in Table 1.

Results were evaluated as follows: Apoptotic and PR responses are expressed in terms of a ratio or percentage of the corresponding response obtained in untreated replicate cultures. A desirable response would be simultaneous maximal reduction of Apoptotic cell count and enhancement of PR cell count. Therefore, the responses are then ranked according to each lot's respective response for each variable as shown in Table 2.

TABLE 2

Analysis of results of screening data
Activity determined at 10 nM TPA

|   | serum lot # | rank | Suppression of apoptosis | rank | Induction of prot-R | total ranking |
|---|---|---|---|---|---|---|
|   | 1 | 3 | 58.0 | 2 | 272 | 5 |
|   | 2 | 1 | 44.1 | 5 | 207 | 6 |
| X | 3 | 2 | 50.0 | 1 | 296 | 3 |
|   | 4 | 4 | 60.2 | 4 | 208 | 8 |
|   | 5 | 5 | 62.5 | 3 | 263 | 8 |

The results shown in Table 2 indicate that Lot #3 ranked second in suppression of apoptotic cells, and first in induction of trypsin resistance. This sum of 3 was then determined to be the best of the five lots evaluated and it was then selected for use in the peptide assay described in Example 3.

Example 3

Assay of Putative Therapeutic Peptide Mixtures

In order to determine whether the assay described in Example 1 was effective in recognizing agents with potential therapeutic activity, the following assay was performed utilizing peptide mixtures. The assay was performed essentially as described in. Example 1 with C3H-10T1/2 clone 8 with the addition of various peptide mixtures. The peptides utilized were obtained from soy beans and designated pp/g, EDI, ARD, FXP, GS90FB, pp750, SPH, PRO (commercially available from such sources as Arthur Daniels Midland and Purina); and a protein product obtained from peas and designated PEA commercially available from such companies as Grinsted and Novo Nordisk.

The cells were used during exponential growth phase when cell cycle position is randomly distributed with no cells arrested in $G_0$. At T=0, cultures are transferred to serum-free medium as an apoptosis stimulus controls included 1 nM TPA to ensure responsiveness of cell cultures, and acetone as a non-specific solvent control.

Peptide mixtures were added to serum-free medium at the highest concentration previously determined to exhibit no toxicity as determined by suppression of cloning efficiency in a conventional cytotoxicity assay. Toxicity was determined by detection of a statistically significant suppression of cell cloning efficiency when the agents were added to cell cultures 24 h after seeding at 200 cells per 20 square centimeter culture plate. Assays were performed on 4 replicate culture plates and consisted of counting the number of clones of greater than 16 cells at day 7.

Only three peptide mixtures were found to be toxic at 1:10 dilution levels of the saturated stock solutions: pp750; SPH; and PRO. At 1:100 and 1:1000 dilution levels, none of the peptides were found to be toxic. Analyses of cell responses are made at either 24 hours (FIG. 2 and Table 3) or 48 hours (FIG. 3 and Table 4) after serum deprivation.

Three measurements were performed on each culture plate consisting of differential cell counts:

1. Apoptotic cell count: These released cells consist of >95% apoptotic cells as shown by both ultrastructure analysis and DNA fragmentation analysis.

2. Proteinase resistant cell count: The fraction of cells that are resistant to proteinase-release is counted. These cells represent the subpopulation that responds to the apoptosis inhibitor TPA and contains the mitogenic responsive cells. Research indicates that this population is critical to control of apoptosis, probably through mechanisms related to modulation of gene expression through mechanisms related to cell shape and adhesion to substrates. This response has been shown to be related but independent of simple suppression of apoptotic cell number. It remains a critical but empirical marker for apoptosis modulation.

3. Proteinase-sensitive cell count: This is the remaining fraction of the total cell population which exhibits high sensitivity to proteinase release from adhesion surface. At present this count is used to calculate the total cell number in each plate in order to determine whether the agent had mitogenic properties.

Figure 2:
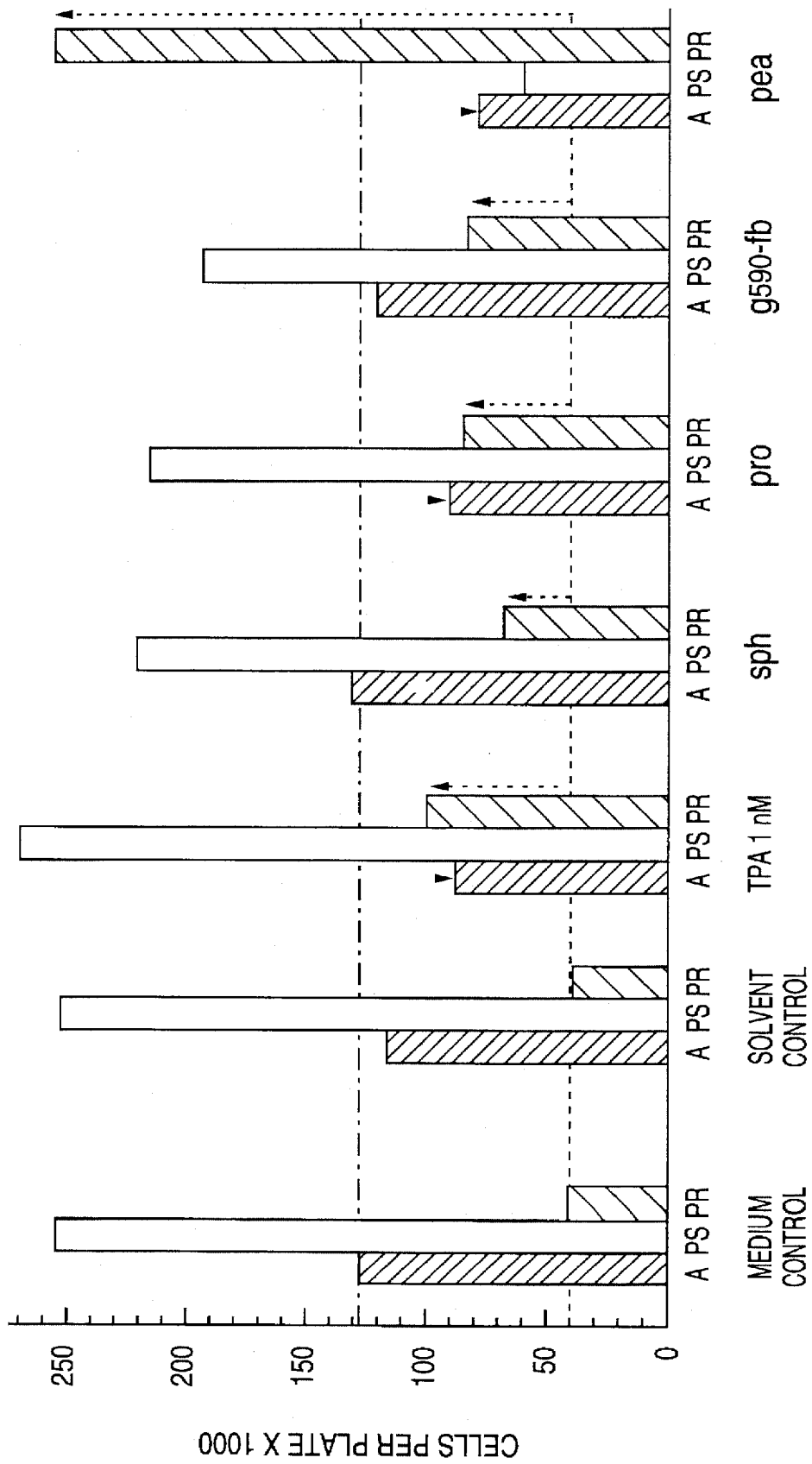
FIG. 2 is a bar graph depicting apoptotic/trypsin sensitive/trypsin resistant cell count analysis at 24 hours post serum-deprivation.

The results obtained are shown in FIGS. 2 and and Tables 3 and 4.

TABLE 3

Experiment 158
Effects Determined at 24 hours

| (SD) | medium control | solvent control | TPA 1 nM | sph | pro | g590-fb | pea |
|---|---|---|---|---|---|---|---|
| Apo | 126.8 (15.7) | 114.2 (23.1) | 85.9 (11.0) | 130.9 (15.7) | 90.9 (18.2) | 122.5 (27.0) | 78.0 (11.2) |
| PS | 254.7 (11.6) | 253.3 (2.6) | 271.6 (17.4) | 222.2 (31.7) | 218.2 (29.2) | 196.9 (25.9) | 63.3 (6.0) |
| PR | 39.2 (4.8) | 36.2 (4.0) | 99.0 (33.5) | 66.0 (5.9) | 83.7 (4.5) | 83.7 (16.2) | 261.5 (12.0) |
| Total | 420.7 | 403.7 | 456.5 | 419.1 | 392.8 | 403.1 | 402.8 |

TABLE 4

Experiment 158
Effect determined at 48 hours

|       | medium | solvent | TPA 1 nM | sph   | pro   | g590-fb | pea   | sph (+) | pro (+) | pea (+) | g590-fb (+) |
|-------|--------|---------|----------|-------|-------|---------|-------|---------|---------|---------|-------------|
| Apo   | 126.4  | 105.1   | 54.1     | 100.2 | 79.2  | 34.8    | 141.3 | 89.8    | 62.1    | 103.2   | 58.2        |
| PS    | 150.2  | 115.2   | 43.3     | 136.6 | 118.4 | 112.7   | 29.8  | 58.4    | 59.2    | 24.8    | 45.8        |
| PR    | 92.5   | 105.8   | 306.7    | 72.6  | 96.1  | 103.6   | 178.4 | 242.2   | 232.8   | 240.7   | 248.4       |
| Total | 369.1  | 326.1   | 404.1    | 309.4 | 293.7 | 251.1   | 349.5 | 390.4   | 354.1   | 368.7   | 352.4       |

TABLE 5

Experiment 163

|                  | control     | acetone     | SE90F       | Alanate-166 1:1000 | Alante-166 1:1000 | Alante-166 1:100 | TPA         |
|------------------|-------------|-------------|-------------|--------------------|-------------------|------------------|-------------|
| Apo              | 14/1 (1.1)  | 15.3 (1.5)  | 10.8 (2.3)  | 4.6 (0.4)          | 9.2 (0.7)         | 6.3 (0.4)        | 21.7 (0.7)  |
| PS               | 27.1 (1.5)  | 17.8 (1.3)  | 27.8 (8.5)  | 25.4 (4.7)         | 22.3 (5.2)        | 29.4 (5.1)       | 19.6 (2.3)  |
| PR               | 39.8 (3.7)  | 46.1 (4.5)  | 31.3 (0.6)  | 46.8 (5.9)         | 43.8 (1.7)        | 50.2 (1.7)       | 61.1 (5.2)  |
| Total cells/plate| 81.3        | 79.2        | 69.9        | 76.8               | 75.3              | 85.9             | 102.4       |

TABLE 6

Experiment 157: Peptide mixtures in presenence and absence of TPA Cells per culture plate × 1000

| +/−1 nM TPA     | Apo   | PS    | PR    | Total | mito-genic | apo inhibition | PR activity |
|-----------------|-------|-------|-------|-------|------------|----------------|-------------|
| medium control  | 140.1 | 30.50 | 177.1 | 347.7 |            |                |             |
| solvent control | 173.0 | 35.15 | 187.0 | 395.2 |            |                |             |
| TPA 1 nM        | 125.1 | 24.80 | 293.4 | 443.6 | yes        | yes            | yes         |
| pro(−)          | 91.3  | 25.60 | 162.5 | 289.4 | no         | yes            | no          |
| pro(+)          | 63.1  | 32.80 | 226.4 | 322.2 |            |                |             |
| pp 750(−)       | 112.2 | 26.60 | 189.9 | 328.7 | no         | yes            | no          |
| pp 750(+)       | 73.3  | 21.40 | 210.9 | 304.6 |            |                |             |
| g590-fb(−)      | 40.2  | 36.40 | 182.6 | 259.1 | no         | yes            | no          |
| g590-fb(+)      | 73.4  | 27.60 | 256.4 | 357.4 |            |                |             |
| pea(−)          | 92.0  | 20.40 | 182.8 | 298.2 | no         | yes            | no          |
| pea(+)          | 126.2 | 24.00 | 216.7 | 367.0 |            |                |             |
| pp 16-10(−)     | 226.0 | 13.40 | 206.0 | 447.3 | yes        | no             | no          |
| pp 16-10(+)     | 187.7 | 12.10 | 295.3 | 497.1 |            |                |             |
| fxp 720(−)      | 231.4 | 11.10 | 196.4 | 438.9 | yes        | no             | no          |
| fxp 720(+)      | 204.3 | 13.30 | 279.3 | 496.9 |            |                |             |
| ard(−)          | 201.9 | 16.30 | 206.7 | 424.9 | yes        | no             | no          |
| ard(+)          | 180.2 | 18.50 | 276.7 | 478.5 |            |                |             |
| edi(−)          | 151.5 | 19.20 | 146.5 | 317.2 | no         | no             | no          |
| edi(+)          | 131.0 | 17.60 | 205.1 | 353.6 |            |                |             |

Figure 3:
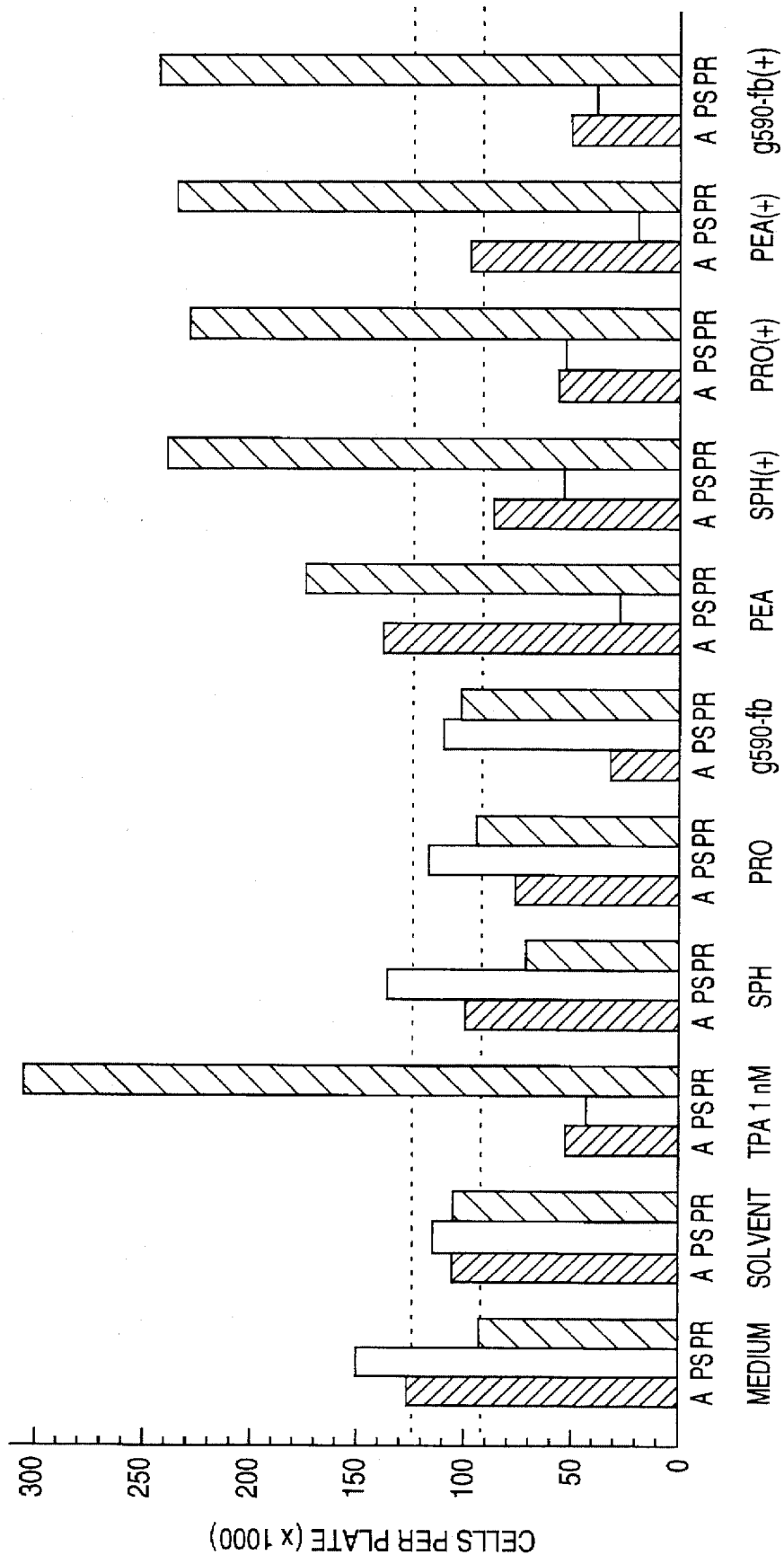
FIG. 3 is a bar graph depicting apoptotic/trypsin sensitive/trypsin resistant cell count analysis at 48 hours post serum-deprivation.
Figure 4:
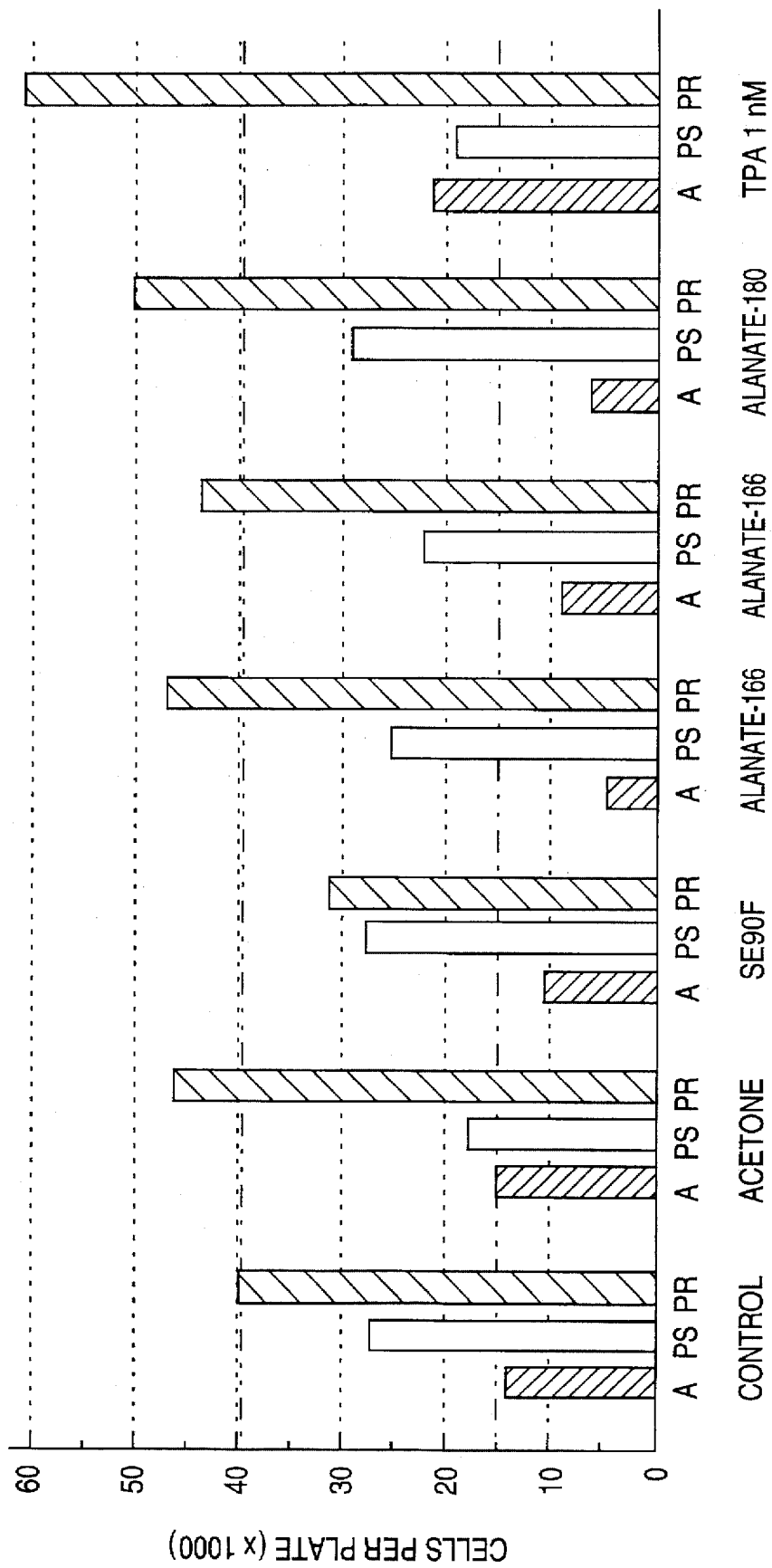
FIG. 4 is a bar graph depicting apoptotic/trypsin sensitive/trypsin resistant cell count analysis at 24 hours post serum-deprivation of SF90, alanate 166, and alanate 180.

As determined by the results depicted in Tables 3–6 and FIGS. 2–4, the activities of the peptide mixtures were as follows:

1. No Activity. Defined as having no appreciable effect on any measurement at concentrations of 1:10, 1:100, and 1:1000. Peptide mixtures exhibiting no activity included SE90F and EDI;

2. Anti-apoptotic. Defined as being active at either 24 or 48 hours post serum deprivation in significantly depressing the number of apoptotic cells in each plate. Peptide mixtures exhibiting anti-apoptotic activity included: PRO (1:10, 1:100); pp750 (1:100); gs90fb (1:10); PEA (1:10); Alanate 166 (1:100, 1:1000); and Alanate 180 (1:100);

3. PR induction. Defined as able to induce significantly increased proteinase-resistant adhesion. Peptide mixtures exhibiting PR induction include: PEA (1:10); Alanate 180 (1:100); and SPH (1:1000); and 4. Mitogenic: Defined as able to significantly increase the total cell number 24 hours after addition to serum-free medium. Peptides exhibiting mitogenic activity include: pp16–10 (1:10); fxp-720 (1:10); and ARD (1:10).

It should be noted that only PEA and alanate-180 were found to have activity in two measurements, Anti-apoptotic activity and PR induction activity. Although neither was mitogenic, PEA also did not interfere with TPA mitogenicity when added in combination.

It has also been found that agents may effect apoptosis at 24 or 48 hours. Consequently, it is preferable to analyze the effect of putative therapeutic agents at both 24 and 48 hours.

Example 4

Statistical Analysis of Screening Assay

In order to determine the requisite sample size to assure statistically significant results, the results presented in Tables 3 and 4 were recompiled and subject to statistical analysis. The statistical analysis was performed as described in Daniel, *Biostatistics: A Foundation in the Health Sciences.*, 2 ed. John Wiley and Sons (1978). The results of the assessment of statistical significance of sample size are presented in Table 7.

Typical results were used including mean values and standard deviation of the means from actual assay measurements obtained as previously described by Daniel (1978). Mean values of both control and peptide-treated groups and their respective standard deviations are tabulated followed by sample sizes of either 2 or 4 replicate culture plates. Based upon choices of culture replicate values of either 2 or 4, statistics were calculated and levels of significance were determined. The levels of significance were evaluated by selecting the lowest value of replicates that provided statistical reliability as determined by p values of 0.050 or less in order to provide general statistical reliability at the 95% confidence level.

In Table 7, examples 1–12 are results obtained with G590-FB at 24 hours (1–6) and 48 hours (7–12) respectively; examples 13–24 are those obtained with TPA at 1 nM at 24 hours (13–18) and 48 hours (19–24) respectively; and examples 25–36 are those obtained with PEA proteins at 24 hours (25–30) and 48 hours (31–36) respectively.

TABLE 7

STATISTICAL ASSESSMENT OF METHODOLOGIES TO IDENTIFY POSSIBLE APOPTOSIS MODULATING PEPTIDES

| | SAMPLE CONTROL MEAN | PEPTIDE MEAN | CONTROL SD | PEPTIDE SD | CONTROL SAMPLE SIZE | PEPTIDE SAMPLE SIZE | EQUAL VARIANCE TEST: F STAT | EQUAL VARIANCE TEST: P-VALUE | POOLED VARIANCE | TEST | T STAT | DF | P-VALUE |
|---|---|---|---|---|---|---|---|---|---|---|---|---|---|
| 1. | 126.8 | 122.5 | 15.7 | 27 | 2 | 2 | 2.95752 | 0.67060 | 487.745 | = | 0.19470 | 2.00000 | 0.86361 |
| | | | | | | | | | | ≠ | 0.19470 | 1.60686 | 0.86738 |
| 2. | 126.8 | 122.5 | 15.7 | 27 | 4 | 4 | 2.95752 | 0.39693 | 487.745 | = | 0.27535 | 6.00000 | 0.79228 |
| | | | | | | | | | | ≠ | 0.27535 | 4.82058 | 0.79446 |
| 3. | 254.7 | 196.9 | 11.6 | 25.9 | 4 | 4 | 4.98521 | 0.21988 | 402.685 | = | 4.07343 | 6.00000 | 0.006550 |
| | | | | | | | | | | ≠ | 4.07343 | 4.15700 | 0.014041 |
| 4. | 254.7 | 196.9 | 11.6 | 25.9 | 2 | 2 | 4.98521 | 0.53614 | 402.685 | = | 2.88035 | 2.00000 | 0.10236 |
| | | | | | | | | | | ≠ | 2.88035 | 1.38567 | 0.15346 |
| 5. | 39.2 | 83.7 | 4.8 | 16.2 | 4 | 4 | 11.3906 | 0.075934 | 142.74 | = | −5.26747 | 6.00000 | .0018878 |
| | | | | | | | | | | ≠ | −5.26747 | 3.52272 | .0087946 |
| 6. | 39.2 | 83.7 | 4.8 | 16.2 | 2 | 2 | 11.3906 | 0.36676 | 142.74 | = | −3.72466 | 2.00000 | 0.06512 |
| | | | | | | | | | | ≠ | −3.72466 | 1.17424 | 0.13736 |
| 7. | 126.4 | 34.8 | 15.6505 | 7.67020 | 4 | 4 | 4.16333 | 0.27195 | 151.885 | = | 10.5112 | 6.00000 | .00004356 |
| | | | | | | | | | | ≠ | 10.5112 | 4.36254 | .00029166 |
| 8. | 126.4 | 34.8 | 15.6505 | 7.67020 | 2 | 2 | 4.16333 | 0.58020 | 151.885 | = | 7.43256 | 2.00000 | 0.017625 |
| | | | | | | | | | | ≠ | 7.43256 | 1.45418 | 0.039426 |
| 9. | 150.2 | 112.7 | 6.84068 | 14.8244 | 4 | 4 | 4.69632 | 0.23614 | 133.279 | = | 4.59372 | 6.00000 | .0037165 |
| | | | | | | | | | | ≠ | 4.59372 | 4.22218 | .0088637 |
| 10. | 150.2 | 112.7 | 6.84068 | 14.8244 | 2 | 2 | 4.69632 | 0.55046 | 133.279 | = | 3.24825 | 2.00000 | 0.08313 |
| | | | | | | | | | | ≠ | 3.24825 | 1.40739 | 0.12950 |
| 11. | 92.5 | 103.6 | 11.3265 | 20.0516 | 4 | 4 | 3.13404 | 0.37322 | 285.179 | = | −0.96398 | 6.00000 | 0.37228 |
| | | | | | | | | | | ≠ | −0.96398 | 4.73756 | 0.38164 |
| 12. | 92.5 | 103.6 | 11.3265 | 20.0516 | 2 | 2 | 3.13404 | 0.65468 | 265.179 | = | −0.68164 | 2.00000 | 0.56581 |
| | | | | | | | | | | ≠ | −0.68164 | 1.57919 | 0.58154 |
| 13. | 254.7 | 271.6 | 11.6 | 17.4 | 2 | 2 | 2.25 | 0.74867 | 218.66 | = | −1.14288 | 2.00000 | 0.37145 |
| | | | | | | | | | | ≠ | 1.14288 | 1.74227 | 0.38599 |
| 14. | 254.7 | 271.6 | 11.6 | 17.4 | 4 | 4 | 2.25 | 0.52265 | 218.66 | = | −1.61628 | 6.00000 | 0.15716 |
| | | | | | | | | | | ≠ | −1.61628 | 5.22680 | 0.16442 |
| 15. | 39.2 | 99 | 4.8 | 33.5 | 2 | 2 | 48.7088 | 0.18120 | 572.645 | = | −2.49896 | 2.00000 | 0.12970 |
| | | | | | | | | | | ≠ | −2.49896 | 1.04104 | 0.23434 |
| 16. | 39.2 | 99 | 4.8 | 33.5 | 4 | 4 | 48.7088 | .0096292 | 572.645 | = | −3.53406 | 6.00000 | 0.012307 |
| | | | | | | | | | | ≠ | −3.53406 | 3.12313 | 0.036129 |
| 17. | 126.8 | 85.9 | 15.7 | 11 | 2 | 2 | 2.03711 | 0.77814 | 183.745 | = | 3.01728 | 2.00000 | 0.09453 |
| | | | | | | | | | | ≠ | 3.01728 | 1.79114 | 0.10789 |
| 18. | 126.8 | 85.9 | 15.7 | 11 | 4 | 4 | 2.03711 | 0.57382 | 183.745 | = | 4.26708 | 6.00000 | .0052800 |
| | | | | | | | | | | ≠ | 4.26708 | 5.37342 | .0067753 |
| 19. | 126.4 | 54.1 | 15.6505 | 6.92782 | 4 | 4 | 5.10342 | 0.21376 | 146.466 | = | 8.44860 | 6.00000 | .00015014 |
| | | | | | | | | | | ≠ | 8.44860 | 4.13221 | .00093096 |
| 20. | 126.4 | 54.1 | 15.6505 | 6.92782 | 2 | 2 | 5.10342 | 0.53060 | 146.466 | = | 5.97406 | 2.00000 | 0.026894 |
| | | | | | | | | | | ≠ | 5.97406 | 1.37740 | 0.059835 |
| 21. | 150.2 | 43.3 | 6.84068 | 2.77401 | 4 | 4 | 6.08111 | 0.17235 | 27.2450 | = | 28.9634 | 6.00000 | .0000001122 |
| | | | | | | | | | | ≠ | 28.9634 | 3.96068 | .0000092557 |
| 22. | 150.2 | 43.3 | 6.84068 | 2.77401 | 2 | 2 | 6.08111 | 0.49052 | 27.2450 | = | 20.4802 | 2.00000 | 0.002376 |
| | | | | | | | | | | ≠ | 20.4802 | 1.32023 | 0.012957 |
| 23. | 92.5 | 306.7 | 11.3265 | 103.782 | 4 | 4 | 83.9562 | .0043206 | 5449.53 | = | −4.10350 | 6.00000 | 0.006332 |
| | | | | | | | | | | ≠ | −4.10350 | 3.07146 | 0.025032 |
| 24. | 92.5 | 306.7 | 11.3265 | 103.782 | 2 | 2 | 83.9562 | 0.13841 | 5449.53 | = | −2.90162 | 2.00000 | 0.10108 |
| | | | | | | | | | | ≠ | −2.90162 | 1.02382 | 0.20658 |
| 25. | 126.8 | 78 | 15.7 | 11.2 | 4 | 4 | 1.96500 | 0.59304 | 185.965 | = | 5.06080 | 6.00000 | .0023089 |
| | | | | | | | | | | ≠ | 5.06080 | 5.42531 | .0030906 |
| 26. | 126.8 | 78 | 15.7 | 11.2 | 2 | 2 | 1.96500 | 0.78896 | 185.965 | = | 3.57853 | 2.00000 | 0.069990 |
| | | | | | | | | | | ≠ | 3.57853 | 1.80844 | 0.080999 |
| 27. | 254.7 | 63.3 | 11.6 | 6 | 4 | 4 | 3.73778 | 0.30754 | 85.28 | = | 29.3112 | 6.00000 | .0000001045 |
| | | | | | | | | | | ≠ | 29.3112 | 4.49801 | .0000026126 |
| 28. | 254.7 | 63.3 | 11.6 | 6 | 2 | 2 | 3.73778 | 0.60778 | 85.28 | = | 20.7261 | 2.00000 | .0023198 |
| | | | | | | | | | | ≠ | 20.7261 | 1.49934 | .0079914 |
| 29. | 39.2 | 261.5 | 4.8 | 12 | 4 | 4 | 6.25 | 0.16654 | 83.52 | = | −34.4001 | 6.00000 | .0000000402 |
| | | | | | | | | | | ≠ | −34.4001 | 3.93604 | .0000049874 |
| 30. | 39.2 | 261.5 | 4.8 | 12 | 2 | 2 | 6.25 | 0.48448 | 83.52 | = | −24.3245 | 2.00000 | 0.001686 |
| | | | | | | | | | | ≠ | −24.3245 | 1.31201 | 0.010570 |
| 31. | 126.4 | 141.3 | 15.6505 | 20.2892 | 4 | 4 | 1.68085 | 0.68022 | 328.295 | = | −1.16297 | 6.00000 | 0.28900 |
| | | | | | | | | | | ≠ | −1.16297 | 5.63660 | 0.29170 |

TABLE 7-continued

STATISTICAL ASSESSMENT OF METHODOLOGIES TO IDENTIFY POSSIBLE APOPTOSIS MODULATING PEPTIDES

| | SAMPLE CONTROL MEAN | PEPTIDE MEAN | CONTROL SD | PEPTIDE SD | CONTROL SAMPLE SIZE | PEPTIDE SAMPLE SIZE | EQUAL VARIANCE TEST: F STAT | EQUAL VARIANCE TEST: P-VALUE | POOLED VARIANCE | TEST | T STAT | DF | P-VALUE |
|---|---|---|---|---|---|---|---|---|---|---|---|---|---|
| 32. | 126.4 | 141.3 | 15.6505 | 20.2892 | 2 | 2 | 1.68065 | 0.83657 | 328.295 | = | −0.82235 | 2.00000 | 0.49732 |
| | | | | | | | | | | ≠ | −0.82235 | 1.87887 | 0.50209 |
| 33. | 150.2 | 29.8 | 6.84068 | 2.82464 | 4 | 4 | 5.86503 | 0.18029 | 27.3867 | = | 32.5385 | 6.00000 | .0000000561 |
| | | | | | | | | | | ≠ | 32.5365 | 3.99411 | .0000053961 |
| 34. | 150.2 | 29.8 | 6.84068 | 2.82464 | 2 | 2 | 6.86503 | 0.49859 | 27.3867 | = | 23.0068 | 2.00000 | 0.001884 |
| | | | | | | | | | | ≠ | 23.0068 | 1.33137 | 0.010779 |
| 35. | 92.5 | 178.4 | 11.3265 | 8.18662 | 4 | 4 | 1.91419 | 0.60723 | 97.6555 | = | −12.2931 | 6.00000 | .000017658 |
| | | | | | | | | | | ≠ | −12.2931 | 5.46244 | .000034574 |
| 36. | 92.5 | 178.4 | 11.3265 | 8.18662 | 2 | 2 | 1.91419 | 0.79686 | 97.6555 | = | −8.69250 | 2.00000 | 0.012978 |
| | | | | | | | | | | ≠ | −8.69250 | 1.82081 | 0.017160 |

The results obtained from the statistical analysis indicate that the sample size is critical to obtaining statistically significant results. Changing the sample number from 4 to 2 results in a statistically significant change in both the P and T values. Thus, it is preferred that a sample size of at least 4 be utilized in order to obtain statistically significant results.

I claim:

1. A method of identifying potentially therapeutically effective agents comprising determining the ability of the agents to alter the proteinase sensitivity of apoptosis sensitive cells exposed to apoptotic agents, wherein the agent is determined to have potential therapeutic efficacy if the apoptosis of the cells in response to the agents changes compared to control cells not exposed to the agent.

2. A method for screening agents for potential therapeutic efficacy comprising the steps of:
   a) culturing a cell strain that is sensitive to apoptotic agents for a time sufficient to attain exponential proliferation without density dependent constraints;
   b) exposing the cell strain to a condition that induces apoptosis;
   c) exposing the cell strain to an agent to be screened;
   d) culturing the cell strain for a time and under conditions suitable to maintain exponential proliferation without density dependent constraints;
   e) removing and enumerating cells that display diminished adherence to yield adherent cells;
   f) exposing the adherent cells to a proteinase for a time and under conditions suitable to release proteinase sensitive cells;
   g) removing and enumerating the proteinase sensitive cells to yield proteinase resistant cells;
   h) incubating the proteinase resistant cells for a time and under a condition suitable to release the cells; and
   i) collecting and enumerating the proteinase resistant cells;
   wherein the agent is determined to have potential therapeutic efficacy if the number of non-adherent cells is reduced relative to the number of non-adherent cells in a control, and the number of proteinase resistant cells increases relative to a control.

3. The method according to claim 2 wherein the cell strain is a pluripotent embryonic cell with a stable, normal, intact, phenotype.

4. The method according to claim 2 wherein the cell strain exhibits density dependent regulation of proliferation and death; is pluripotent; is sensitive to transformation induced by carcinogenic and oncogenic agents; responds to agents that under suitable conditions either induce or block proliferation, differentiation, and apoptosis; and exhibits apoptotic cell death.

5. The method according to claim 4 wherein apoptosis of the cell strain comprises ultrastructural changes of chromatin and changes in the molecular structure of DNA which changes are associated with apoptotic DNA degradation.

6. The method according to claim 2 wherein the cell strain is C3H-10T1/2 clone 8.

7. The method according to claim 2 wherein the initial step of capturing to attain exponential proliferation without density dependent constraints is for about 5 days at 37° C. with a gas overlay of 5% $CO_2$ in a suitable growth medium.

8. The method according to claim 2 wherein the condition that induces apoptosis is serum deprivation, growth factor deprivation, ultraviolet radiation, γ-radiation, soft β-radiation, hypo-osmotic shock, chemotherapeutic agents or specific receptor mediated agents.

9. The method according to claim 8 wherein the culturing in step (d) continues for a time and under conditions suitable to attain a density of about one population density doubling from density-dependent arrest of cell cycle.

10. The method according to claim 9 wherein the culturing is for about 5 days at 37° C. with 5% $CO_2$.

11. The method according to claim 2 wherein the proteinase is trypsin.

12. The method according to claim 2 wherein the adherent cells are incubated in the presence of concentrations of about 1 μg/ml to 1 mg/ml trypsin for about 10 minutes with gentle shaking at room temperature and are removed by gentle shearing effected by washing.

13. The method according to claim 2 wherein the proteinase resistant cells are released by incubation in the presence of an agent that decreases the calcium concentration to a level sufficient to release the cells.

14. The method according to claim 13 wherein the agent that decreases the calcium concentration is a calcium chelator.

15. The method according to claim 14 wherein the calcium chelator is selected from the group consisting of ethylenediaminetetraacetic acid and ethylene glycol-bis(β-amino-ethyl ether) N,N,N',N'-tetraacetic acid.

16. A method of screening agents for potential therapeutic efficacy comprising the steps of:
   a) culturing cell strain C3H-10T½ for a time and under conditions sufficient to attain stable exponential proliferation without density dependent constraints;

b) exposing the cell strain to a condition that induces apoptosis;

c) exposing the cell strain to an agent to be screened simultaneously with apoptosis induction or shortly thereafter;

d) culturing the cell strain for a time and under conditions suitable to maintain a density of about one population doubling fore density dependent arrest of cell cycle;

e) removing and enumerating cells that display diminished adherence to yield adherent cells;

f) incubating the adherent cells for a time and under conditions suitable to release proteinase sensitive cells;

g) removing and enumerating the proteinase sensitive cells to yield proteinase resistant cells;

h) incubating the proteinase resistant cells for a time and under a condition suitable to release the cells; and i) collecting and enumerating the proteinase resistant cells;

wherein the agent is determined to have potential therapeutic efficacy if the ratio of proteinase sensitive cells to proteinase resistant cells changes relative to a control.

* * * * *